United States Patent [19]

Vinegar

[11] 4,438,142
[45] Mar. 20, 1984

[54] PHARMACEUTICAL COMBINATION

[75] Inventor: Ralph Vinegar, Chapel Hill, N.C.

[73] Assignee: Burroughs Wellcome Co., Research Triangle Park, N.C.

[21] Appl. No.: 418,979

[22] Filed: Sep. 16, 1982

Related U.S. Application Data

[63] Continuation-in-part of Ser. No. 354,160, Mar. 5, 1982.

[51] Int. Cl.$^3$ .......................................... A61U 31/485
[52] U.S. Cl. .................................................. 424/260
[58] Field of Search ........................................ 424/260

[56] References Cited

PUBLICATIONS

Chem. Abst., vol. 84-30878u (1976).

*Primary Examiner*—Stanley J. Friedman
*Attorney, Agent, or Firm*—Donald Brown

[57] ABSTRACT

This invention relates to combinations of codeine and the compound of Formula (I)

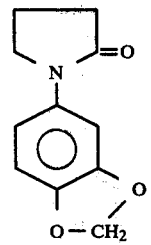

I as well as pharmaceutical formulations containing the combination and the use of such combination in medicine. It has been found that the analgesic properties of codeine are significantly potentiated by the combination with compound of Formula (I).

8 Claims, No Drawings

PHARMACEUTICAL COMBINATION

This application is a continuation-in-part of application Ser. No. 354,160 filed Mar. 5, 1982.

This invention relates to pharmaceutical combinations, formulations comprising the combinations and the use of such combinations and formulations in medicine.

In particular, this invention relates to pharmaceutical combinations in which one of the ingredients of the combination potentiates the pharmacological activity of another ingredient of the combination. In such combinations, the first-mentioned ingredient is often referred to as a potentiator or synergist (in respect of the second-mentioned active ingredient). One of the advantages of combining the use of a synergist with the use of an active ingredient is that, for exhibiting a certain level of pharmacological activity, less active ingredient is required when administered in combination with the synergist compared with the dose of active ingredient required in the absence of the synergist.

It has now been found that the well-known analgesic activity of codeine and its pharmaceutically-acceptable salts (hereinafter collectively referred to as 'codiene') is potentiated to a surprising degree by the compound of formula (I), namely, 1-(1,3-benzodioxol)-5-yl-2-pyrrolidinone, hereinafter referred to as 'compound I'.

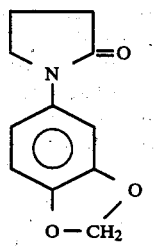

(I)

For example, upon oral administration, compound I potentiated the analgesic activity of codeine by in the range of from four to seven times; therefore, the amount of codeine usually (i.e. absence compound I) administered orally can be reduced by a corresponding factor.

Therefore, this invention provides a pharmaceutical combination comprising codeine in association with a synergistic amount of compound I, (hereinafter referred to as "the combination"). Clearly, the more convenient forms for (especially oral) administration of the combination are those wherein the codeine and compound I are intimately mixed. However, the combination may be administered by the separate administration of both codeine and compound I provided that this allows in vivo admixture of the codeine with a synergistic amount of compound I.

The combination may be used in conditions similar to the usual uses of codeine (i.e. absent compound I). This invention therefore further provides a pharmaceutical combination for use in the relief, treatment or prophylaxis of pain (moderate to severe) in a mammal, including man, such as: that resulting from headache, toothache, pain following general dental procedures, oral and general surgery, dysmenorrhea, myalgia, pain of unresectable cancer, joint, central and peripheral nerve disorders, acute flare-ups of rheumatoid and osteoarthritis and other conditions associated with pain; and as an antitussive agent.

The ratio of codeine to compound I may vary from about 1:10 to about 1:50 but the ratio of 1:25 is preferred. The amount of a combination of codeine and compound I for the treatment of the above conditions will, of course, vary with condition and the patient under clinical treatment, and is ultimately at the discretion of the physician. However, a suitable analgesic dose of the combination preferably comprises in the range of from 4 mg of codeine in association with 100 mg of compound I to 60 mg of codeine in association with 1500 mg of compound I administered every 4 hours. More preferably, the range is from 8 mg codeine/200 mg compound I to 24 mg codeine/600 mg compound I. For example, a typical dose for a human receipient is 12 mg of codeine in association with 300 mg of compound I administered at 4 hourly intervals; this combination elicits the degree of analgesia produced by 1 grain (65 mg) of codeine alone, and anti-inflammatory and antipyretic benefits imparted by compound I may also be realized from this combination.

While it is possible for the combination to be administered with the ingredients in the form of the raw chemicals, it is preferable to present the ingredients as one or more pharmaceutical formulation(s). Formulations of the present invention, both for veterinary and for human medical use, comprise the combination together with a pharmaceutically acceptable carrier therefor and optionally any other therapeutic ingredient(s). The carrier(s) must be pharmaceutically acceptable in the sense of being compatible with the other ingredients of the formulation and not deleterious to the recipient thereof. The other therapeutic ingredient(s) may include other analgesics, anti-inflammatories or antipyretics. The more convenient formulations of the combination are those wherein the codeine and compound I are intimately mixed together with the carrier, resulting in a single formulation for administration in the desired manner. However, the combination may be administered by the separate administration of both a formulation of codeine and a (similar or different) formulation of compound I provided that this allows in vivo admixture of the codeine with a synergistic amount of compound I; this latter type of formulation of the combination may be presented as a multi-component pack comprising the codeine in intimate physical juxtaposition to the compound I, one or both of which may either be admixed with a carrier or in intimate physical juxtaposition to a carrier, together with written instructions as to the administration of the components.

Formulations of the present invention include those suitable for oral or rectal. Formulations for rectal administration may be presented as a suppository with a usual carrier such as cocoa butter. The formulations may be prepared by any of the methods well known in the art of pharmacy. All methods include the step of bringing the combination, preferably comprising an intimate mixture of codeine and compound I, into association with a carrier which constitutes one or more accessory ingredients. In general, the formulations are prepared by uniformly and intimately bringing the combination into association with a liquid carrier or a finely divided solid carrier or both and then, if necessary, shaping the product into the desired formulation.

Formulations of the present invention suitable for oral administration may be presented as discrete units such as capsules, cachets, tablets or lozenges, each containing a predetermined amount of the combination; as a power or granules; or a suspension in an aqueous liquid or non-aqueous liquid such as a syrup, an elixir, an emulsion or a draught.

A tablet may be made by compression or moulding, optionally with one or more accessory ingredients. Compressed tablets may be prepared by compressing in a suitable machine, the combination being in a free-flowing form such as a powder or granules, optionally mixed with a binder, lubricant, inert diluent, surface active or dispersing agent. Moulded tablets may be made by moulding in a suitable machine, comprising a mixture of the powdered combination with any suitable carrier.

A syrup may be made by adding the combination to a concentrated, aqueous solution of a sugar for example sucrose to which may also be added any accessory ingredient. Such accessory ingredients may include flavourings, an agent to retard crystallization of the sugar or an agent to increase the solubility of any other ingredient, such as a polyhydric alcohol for example glycerol or sorbitol.

In addition to the aforementioned ingredients, the formulations of this invention may further include one or more accessory ingredient(s) selected from diluents, buffers, flavouring agents, binders, surface active agents, thickeners, lubricants, preservatives (including antioxidants) and the like.

Compound I may be prepared by any method known in the art for the preparation of compounds of analogous structure. For Example, a method for preparing compound I comprises cyclisation, as hereinafter described, of a compound of formula (II) or a compound of formula (III):

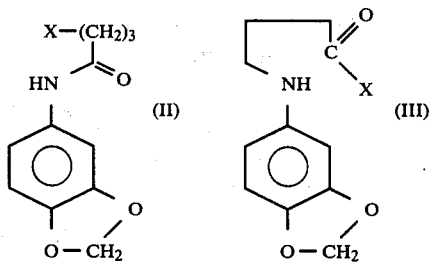

wherein X is a standard leaving group (J. March, Advanced Organic Chemistry, 2nd Ed., page 187, New York (1977)) such as halide for example chloride or bromide, hydroxide, $-OR^1$, imidazolyl, sulphoxonium or tosyl; and $R^1$ is hydrogen or alkyl of 1 to 4 carbon atoms, preferably ethyl. Preferred compounds of formula (II) are those wherein the leaving group is a halide (such as chloride or bromide), hydroxide or tosyloxy, and preferred compounds of formula (III) are those wherein the leaving group is $-OR^1$ as defined. A particularly preferred method comprises cyclisation of a compound of formula (II) as hereinbefore defined, especially wherein X is chloride.

Cyclisation may be effected at room temperature or with heating, for example at a temperature of 155°–220° C., optionally in an oxygen-free atmosphere, for example in nitrogen, optionally in an inert solvent such as tetrahydrofuran, dichloromethane, diethyl ether, tert-butanol, xylenes, or toluene, and optionally with a catalyst. The catalyst chosen will depend on the compound of formula (II) or (III) to be cyclised; for example, where the reaction involves elimination of an acid such as hydrochloric and, a basic catalyst may be used with or without a solvent such as water or an alcohol such as butanol optionally, but preferably, in the presence of a phase transfer catalyst such as triethylbenzyl ammonium chloride with or without a solvent such as dichloromethane, diethyl ether, zylenes or toluene, but preferably dichloromethane. Examples of suitable basic catalysts are: an alkali metal hydride, hydroxide, alkoxide or amide such as potassium or sodium hydride, potassium or sodium hydroxide, potassium tert-butoxide or lithium di-isopropylamide. The most preferred method of cyclisation is effected by using aqueous sodium hydroxide in the presence of triethylbenzyl ammonium chloride at room temperature.

Where X is a slow or poor leaving group cyclisation may take place by conversion in situ to a further or better leaving group. For example where X is hydroxide, tosyl chloride may be present in the reaction mixture in order that the tosyloxy group (a better leaving group) is substituted for the hydroxide group thereby causing cyclisation to proceed faster and more completely.

Examples I and A to D are provided by the way of illustration of the present invention and should in no way be construed as a limitation thereof.

EXAMPLE 1

Preparation of 1-(2,3-Benzodioxol-5-yl)-2-pyrrolidinone

A mixture of 3,4-(methylenedioxy)aniline (200 g, 1.46 mole) and Y-butyrolactone (225 ml) was heated (in a dry nitrogen atmosphere) with stirring in a 200° oil bath for 2 days. Product was isolated from the reaction mixture by distillation under reduced pressure (bp 156° C., 33 u). Product was filtered through Silica Gel 60 (Trade Name) eluting with ethyl acetate. The eluant was concentrated and the crystalline product was collected and washed with diethyl ether and petroleum ether affording 1-(1,3-benzodioxol-5-yl)-2-pyrrolidinone (153.4 g; 51%) mp 89°–91° C. which was one spot on tlc analysis.

Elemental analysis: Calculated for $C_{11}H_{11}NO_3$: C, 64.36%; H, 5.40%; N, 6,83%. Found: C, 64.30%; H, 5.33%; N, 6.8%.

EXAMPLE I

Analgesic Activity: Rat Hot Plate Assay

The rat hot plate assay incorporated two modifications of the mouse hot plate assay originally described by Eddy et al., J. Pharmacol. Exp. Ther. 98, 121–137 (1950). The first modification was enlargement of the diameter of the cylindrical (water filled) copper plate to 25.0 cm to accommodate rats instead of mice. The second modification was the use of a temperature controller to regulate a 250 watt infrared heat lamp which was activated via a thermistor probe attached to the under surface of the copper plate, the temperature of which was thus maintained at 45±1.0° C. (N=28 measurements of the plate temperature under experimental conditions). The time required for a rat placed on the hot plate to respond by lifting, shaking or licking either of its hind or forelimbs was recorded in tenths of a second. Only animals responding in pretest within 6–13 seconds were used in the studies. The combination, comprising an intimate mixture of codeine phosphate with compound I, was suspended in 0.5% sodium carboxymethylcellulose and administered orally, by gavage, in a volume of 1.00 ml/100 g.b. wt. 60 min prior to testing. Animals which responded in less than 18.3 seconds were considered unprotected and those which did not respond within 18.3 seconds were considered protected. The reaction time of 18.3 seconds represented the sum of the mean pretest times of 40 untreated rats plus the time of 3 standard deviations of the mean. $ED_{50}$'s and their standard errors were estimated from a graph of the dose-response curves using the method of Miller and Tainter (Proc. Soc. Exp. Biol. Med. 57, 261–262 (1944). Following this procedure the analgesic activities of codeine, compound I and the combination (codeine + compound I) were compared (Table I).

TABLE I
RESULTS OF HOT PLATE ASSAY

|  | Codeine Phosphate | Compound I | Codeine Phosphate + Compound I (50 mg/kg) | Potentate Factor |
|---|---|---|---|---|
| $ED_{50}$ mg/kg, p.o. in rat | 57 ± 35.3 | 86 ± 16.5 | 9.2 ± 30 | 6.2 |

EXAMPLES A TO D

Formulations

| A. TABLET | |
|---|---|
| Compound I | 300.0 mg |
| Codeine Phosphate | 12.0 mg |
| Corn Starch | 20.0 mg |
| Lactose | 85.0 mg |
| Polyvinylpyrrolidone | 3.0 mg |
| Stearic Acid | 6.0 mg |

Compound I and codeine phosphate were sifted and intimately mixed with the powdered excipients, corn starch and lactose. The powders were wetted with an alcoholic solution of polyvinylpyrrolidone to form granules. The granules were dried and mixed with the powdered stearic acid. The formulation was then compressed into tablets weighing approximately 426 mg each.

| B. TABLET | |
|---|---|
| Compound I | 300.0 mg |
| Codeine Phosphate | 12.0 mg |
| Corn Starch | 45.0 mg |
| Microcrystalline Cellulose | 207.0 mg |
| Stearic Acid | 12.0 mg |
| Lactose | q.s. to 360.0 mg |

Compound I and codeine phosphate were sifted and intimately mixed with one-half the powdered excipients, corn starch, microcrystalline cellulose, and stearic acid. The powders were slugged and broken to form granules. The granules were mixed with the remaining corn starch, microcrystalline cellulose, and stearic acid. The formulation was then compressed into tablets weighing approximately 576 mg each.

| C. CAPSULE | |
|---|---|
| Compound I | 300.0 mg |
| Codeine Phosphate | 12.0 mg |
| Corn Starch | 30.0 mg |
| Stearic Acid | 10.0 mg |
| Lactose | q.s. to 360.0 mg |

The finely divided compound I and codeine phosphate were mixed with the powdered excipients lactose, corn starch, and stearic acid and filled into hard-shell, 2-piece gelatin capsules.

| D. ELIXIR | |
|---|---|
| Compound I | 300.0 mg |
| Codeine Phosphate | 12.0 mg |
| Alcohol | 750.0 mg |
| Glycerin | 500.0 mg |
| Propylene Glycol | 1,000.0 mg |
| Sucrose | 2,100.0 mg |
| Flavouring Agent | q.s. |
| Colouring Agent | q.s. |
| Preserving Agent | 0.1% |
| Purified Water | q.s. to 5.0 ml |

Compound I was dissolved in the alcohol and propylene glycol. The codeine phosphate and sucrose were dissolved in the glycerin and a portion of the purified water. The preserving agent was dissolved in another portion of hot purified water, and then the colouring agent was added and dissolved. The three solutions were mixed and cooled before the flavouring agent was added. Purified water was added to adjust the final volume. The resulting elixir was thoroughly mixed.

| E. SUPPOSITORY | |
|---|---|
| Compound I | 300.0 mg |
| Codeine Phosphate | 12.0 mg |
| Cocoa Butter, q.s. or Wecobee Base | 2.0 g |

Wecobee is the trade name or a hydrogenated carboxylic acid.

I claim:

1. An analgesic preparation comprising codeine or a pharmaceutically acceptable salt thereof and 1-(1-3-benzodioxol-5-yl)-2-pyrrolidinone wherein the ratio of codeine or a pharmaceutically acceptable salt thereof to the compound of formula I 1-(1-3-benzodioxal-5-yl)-2-pyrodidinone is in the range of 1:10 to 1:50.

2. A combination of claim 1 wherein the ratio of codeine or a pharmaceutically acceptable salt thereof to the compound of formula I 1-(1-3-bezodioxol-5-yl)-2-pyrrolidinone is 1:25.

3. A formulation according to claim 1, in the form of a capsule, tablet, elixir or suppository.

4. A method for treatment or prophylaxis of pain in a human, comprising the oral or rectal administration to said human of a nontoxic affective analgesic amount of a combination consisting of codeine or a pharmaceutically acceptable salt thereof and 1-(1,3-benzodioxol-5-yl)-2-pyrrolidinone wherein the ratio of codeine or a pharmaceutically acceptable salt thereof to 1-(1,3-benzodioxol-5-yl)-2-pyrrolidinone is in the range of from 1:10 to 1:50.

5. A method of claim 4 wherein the ratio of codeine of a pharmaceutically acceptable salt thereof to 1-(1,3-benzodioxol-5-yl)-2-pyrrolidinone is 1:25.

6. A method of claim 4 or 5 wherein the amount of codeine or a pharmaceutically acceptable salt thereof is in the range of 4 to 60 mg administered every four hours.

7. A method of claim 4 or 5 wherein the amount of codeine is in the range of 8 to 24 mg administered every four hours.

8. A method of claim 4 or 5 wherein the amount of codeine is 12 mg administered every four hours.

* * * * *